United States Patent [19]

Goldenberg

[11] 4,331,647

[45] May 25, 1982

[54] TUMOR LOCALIZATION AND THERAPY WITH LABELED ANTIBODY FRAGMENTS SPECIFIC TO TUMOR-ASSOCIATED MARKERS

[76] Inventor: Milton D. Goldenberg, 11837 Gainsborough Rd., Potomac, Md. 20854

[21] Appl. No.: 126,263

[22] Filed: Mar. 3, 1980

[51] Int. Cl.$^3$ .................... A61K 49/00; A61K 43/00
[52] U.S. Cl. ............................................ 424/1; 424/9
[58] Field of Search ....................................... 424/119

[56] References Cited

U.S. PATENT DOCUMENTS

| | | | |
|---|---|---|---|
| 3,927,193 | 12/1975 | Hansen | 424/1 |
| 4,036,945 | 7/1977 | Haber | 424/1 |
| 4,146,603 | 3/1979 | Davidson et al. | 424/1 |
| 4,234,561 | 11/1980 | Bahl | 424/1 |

OTHER PUBLICATIONS

Quinones et al., J. Nucl. Med., vol. 12, 1971, pp. 69–75.
Hawthorne et al., J. Med. Chem., 15, 449 (1972).
Order, Radiology, 118, 219 (1976).
Ettinger et al., Cancer Treat. Rep., 63, 131 (1979).
Order et al., Int. J. Radiation Oncology Biol. Phys., 6, 703 (1980).
Goldenberg et al., N. Eng. J. Med., 298, 1384 (1978).
Lee et al., Cancer Chemother. Pharmacol., 3, 17 (1979).
Nisonoff et al., Arch. Biochem. Biophys., 89, 230 (1960).
Nisonoff et al., Arch. Biochem. Biophys., 93, 460 (1961).
Nisonoff et al., Nature, 189, 293 (1961).
Porter, Biochem. J., 73, 119 (1959).
Cebra et al., J. Biol. Chem., 236, 1720 (1961).
Hämmerling et al., J. Exp. Med., 128, 1461 (1968).
Bale et al., Cancer Res., 40, 2965 (1980).
Koji et al., Cancer Res., 40, 3013 (1980).
Order et al., Cancer Res., 40, 3001 (1980).

*Primary Examiner*—Christine M. Nucker
*Attorney, Agent, or Firm*—Millen & White

[57] ABSTRACT

Methods are provided for using radiolabeled antibody fragments specific to tumor-associated markers for detection, localization and therapy of tumors. Mixtures of labeled fragments with varied specificity or multivalent hybrid fragments permit detection and localization of more than one tumor or tumor cell type. Antibodies and injectable compositions for use in the methods of the invention are also provided.

50 Claims, No Drawings

TUMOR LOCALIZATION AND THERAPY WITH LABELED ANTIBODY FRAGMENTS SPECIFIC TO TUMOR-ASSOCIATED MARKERS

BACKGROUND OF THE INVENTION

It is known that radiolabeled antibodies specific to antigens which are either produced or associated with tumors can be used to localize tumors. U.S. Pat. No. 3,927,193 to Hansen et al discloses a method of tumor localization using labeled antibodies to carcinoembronic antigen (CEA), but provides examples of its use only in animals. Goldenberg et al, *New Eng. J. Med.*, 298, 1384 (1978), reported success in clinical trials of tumor detection and localization by scintillation scanning of patients receiving radiolabeled antibodies to CEA. A special scanner subtraction technique with other radionuclides to compensate for interstitial and blood-pool background activity was considered essential for unequivocal tumor localization using that method.

However, even this most recent and successful tumor localization and detection process has certain disadvantages which limit its use. The labeled antibodies are very large molecules which also carry cross-reactive antigenic determinants, and it is quite difficult to reduce cross-reactivity below 15% and to achieve specificity for a particular antigen of higher than 70%. The subtraction technique used by Goldenberg et al involves the use of a different radionuclide attached to a carrier having kinetics of transport and distribution different from the labeled specific antibody. In addition, the background-compensating material must be injected prior to each photoscan, which exposes the patient to increased levels of radioactivity and discomfort. A further limitation of the prior art methods is that antibody molecules cannot pass the blood-brain barrier, which means that intravenously injected antibodies cannot be used to localize intracranial tumors. Radioactively labeled fragments obtained by cleavage of antibodies specific to cardiac myosin have been used to determine the location and size of myocardial infarcts, in U.S. Pat. No. 4,036,945 to Haber.

Tumor radiotherapy using labeled antibodies has been suggested by many, and an indication of its success in a single multimodal therapeutic clinical use is reported by Ettinger et al., *Cancer Treat. Rep.*, 63, 131 (1979). The use of the boron-labeled antibodies in therapy is reported by Hawthorne et al., *J. Med. Chem.*, 15, 449 (1972), but the combined incorporation of boron and a radioisotope for localization is not suggested.

A need continues to exist for a rapid, high resolution method of tumor detection and localization, one which ideally is capable of detecting and locating more than one type of tumor or tumor cells using a single injection, and which avoids other disadvantages of the prior art methods.

OBJECTS OF THE INVENTION

Accordingly, it is an object of the present invention to provide a rapid method of tumor localization and detection which achieves high resolution without the necessity of repeated injection of other radioactive material for computer-assisted subtraction of background activity.

Another object of the present invention is to provide antibody fragments for tumor detection and localization having a combination of high specific activity and high specificity for tumor markers, thereby improving the resolution of scintigraphic tumor localization and detection methods. A further object of the invention is to provide multivalent antibody fragments containing in chemical combination fragments having specificity to more than one type of tumor-associated antigen.

Yet another object of the present invention is to provide a method of tumor radiotherapy wherein a radiotherapeutically effective radioisotope is concentrated at the site of tumor growth by virtue of its attachment to an antibody fragment which is highly specific to a tumor-associated marker.

Upon further study of the specification and appended claims, further objects and advantages of this invention will become apparent to those skilled in the art.

SUMMARY OF THE INVENTION

The foregoing objects are achieved by providing a method for detecting and localizing a tumor which either produces or is associated with a cytoplasmic, intracellular or cell-surface marker substance which comprises injecting a subject parenterally with at least one marker-specific fragment obtained by cleavage of an antibody specific to said marker substance and radiolabeled with a pharmacologically inert radioisotope capable of detection using a photoscanning device, and subsequently scanning with said device to detect and locate the site or sites of uptake of said labeled antibody fragment by said tumor.

The invention further provides a method for detecting and localizing at least one type of tumor which either produces or is associated with at least one cytoplasmic, intracellular or cell-surface marker substance, which comprises injecting a subject parenterally with a multivalent hybrid containing in chemical combination at least one marker-specific fragment obtained by cleavage of an antibody specific to a first tumor-associated marker and at least a second, different marker-specific fragment obtained by cleavage of an antibody specific to the same or different tumor-associated marker, said hybrid being radiolabeled with a pharmacologically inert radioisotope capable of detection using a photoscanning device, and subsequently scanning with said device to detect and locate the site or sites of uptake of said labeled hybrid by said at least one type of tumor or tumor cells.

Antibodies and injectable compositions suitable for use in the foregoing methods are provided, as are methods of tumor radiotherapy using radiolabeled marker-specific tumor-associated antibody fragments.

DETAILED DISCUSSION

The marker-specific, labeled antibody fragments used in the method of the present invention are produced by cleavage of antibodies which are specific to a variety of tumor-associated antigens or markers. These may be substances produced by the tumor or may be substances which accumulate on or around tumor cells. They may be intracellular, cell surface or cytoplasmic markers. Among such tumor-associated markers are those disclosed by Herberman, "Immunodiagnosis of Cancer", in Fleisher (ED.), "The Clinical Biochemistry of Cancer", page 347 (Am. Assn. Clin. Chem. 1979) and in U.S. Pat. No. 4,150,149 to Wolfsen et al. Tumor-associated markers have been categorized by Herberman, supra, in a number of categories including oncofetal antigens, placental antigens, oncogenic or tumor virus-associated antigens, tissue-associated antigens, organ-associated antigens, ectopic hormones and normal antigens or variants thereof. Occasionally, a subunit of a tumor-associated marker is advantageously used to raise antibodies having higher tumor-specificity, e.g., the beta-subunit of human chorionic gonadotropin (HCG), which stimulates the production of antibodies having a greatly reduced cross-reactivity to non-tumor substances. Suitable such marker substances to which specific antibodies may be raised which are useful in the present invention include, but are not limited to, alpha-fetoprotein (AFP), human chorionic gonadotropin (HCG) and/or its beta-subunit (HCG-beta), colon-specific antigen-p (CSAp), prostatic acid phosphatase, pancreatic oncofetal antigen, placental alkaline phosphatase, pregnancy $beta_1$-globulin, parathormone, calcitonin, tissue polypeptide antigen, T-antigen, $beta_2$-microglobulin, mammary tumor-associated glycoproteins (MTGP), galactyosyl transferase-II (GT-II), gp-52 viral-associated antigen, ovarian cystadenocarcinoma-associated antigen (OCAA), ovarian tumor-specific antigen (OCA), cervical cancer antigens (CA-58, CCA, TA-4), basic fetoprotein (BFP), terminal deoxynucleotidyl transferase (TdT), cytoplasmic melanoma-associated antigens, human astrocytoma-associated antigen (HAAA), common glioma antigen (CGA), glioembryonic antigen (GEA), glial fibrillary acidic protein (GFA), common meningioma antigen (CMA), ferritin, and tumor angiogenesis factor (TAF).

Marker-specific antibodies may be produced by conventional methods well known in the art. Normally, an animal, preferably a rodent, a rabbit or more preferably a goat or primate is challenged with a tumor-associated marker substance, to which its immune system reacts by producing specific antibodies to these markers. The animal is bled, the immunoblobulin fraction of the blood is isolated, and the specific immunoglobulin isolated by a variety of conventional separation techniques, preferably including one or more affinity chromotography purification steps. Suitable such general methods for raising antibodies specific to tumor-associated marker substances are disclosed inter alia in "Immunodiagnosis of Cancer", Herberman et al, Eds. (Marcel Dekker, Inc., New York and Basel, 1979) and "Cancer Markers," Sell, Ed. (Humana Press, Clifton, N.J., 1980).

Antibodies produced by the foregoing conventional techniques are normally mixtures of antibodies, a certain proportion of which are specific but generally containing a small proportion of antibodies which are cross-reactive with non-tumor-associated antigens. Antibodies purified by repeated affinity chromatography using bound antigens with which some components of the antibody mixture are cross-reactive, as well as passage through a column containing bound purified antigen, have a high specific immunoreactivity, often approaching or even exceeding 70%, and a cross-reactivity with non-tumor associated antigens of less than 15%. These antibodies are considered substantially monospecific to the antigen to which they have been raised, and are preferably used in the present invention.

Highly specific monoclonal antibodies can also be produced by hybridization techniques. Such antibodies normally require little or no purification and normally have a specific immunoreactivity of at least 85%, with specificities of more than 95% in certain cases. Such monoclonal, hybridoma-derived antibodies are also preferred for use in the present invention. In a preferred embodiment, monoclonal antibodies are produced by challenging a monkey with an intracellular tumor-associated marker, fusing antibody-producing monkey lymph or spleen cells with human or mouse myeloma cells to produce hybrid cells which are then isolated, cloned and selected for their ability to produce monoclonal antibodies specific to said marker substance.

Monoclonal antibodies from the immunoglobulin G (IgG) fraction are obtained by the present method, and are used to prepare the fragments used for tumor detection, localization and therapy according to this invention. The IgM monoclonal antibodies of Koprowski, U.S. Pat. No. 4,172,124 are unsuitable for use in the present method. It is known that antibody fragments may be produced by enzymatic cleavage of antobidies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using papain produces two monovalent Fab fragments and an Fc fragment directly. These methods are described inter alia in U.S. Pat. No. 4,036,945 and references contained therein, and in Nisonoff et al, *Arch. Biochem. Biophys.*, 89, 230 (1960); Porter, Biochem. J., 73, 119 (1959); and Edelman et al, in "Methods in Immunology and Immunochemistry", Vol. 1, 422 (Academic Press, 1967).

Other methods of cleaving antibodies, such as further cleavage of Fab fragments or by the use of other enzymatic or chemical techniques may also be used. Only fragments which retain specificity to the tumor-associated marker against which their parent antibodies are raised are used in the present method.

Hybrid antibody fragments have been prepared by oxidative linkage of Fab' fragments resulting from reductive cleavage of different antibodies. A portion of these will contain fragments specific to both of the antigens to which the original antibodies were raised. This is advantageously carried out by mixing two different F(ab')$_2$ fragments produced by pepsin digestion of two different antibodies, reductive cleavage to form a mixture of Fab' fragments, followed by oxidative reformation of the disulfide linkages to produce a mixture of F(ab')$_2$ fragments including hybrid fragments containing an Fab' portion specific to each of the original antigens. Methods of preparing such hybrid antibody fragments are disclosed in Feteanu, "Labeled Antibodies in Biology and Medicine" pages 321-323 (McGraw-Hill Int. Bk. Co., New York et al, 1978); Nisonoff et al, *Arch. Biochem. Biophys.*, 93, 460 (1961); and Hammerling et al, *J. Exp. Med.*, 128, 1461 (1968).

Elimination of the Fc fragment from an antibody to form smaller marker-specific fragments has the advantage of producing a molecule having a lower molecular weight which facilitates mobility of the fragments and their ability to pass through the blood-brain barrier. In addition, the Fc fragment is responsible for the major hyperallergenicity of antibodies and a substantial portion of the non-specific binding. Accordingly, its cleavage reduces the danger of allergic reaction to the injection of antibodies, especially repeated injection for multiple tumor imaging or tumor radiotherapy. Since the kinetics of antibody fragments are more rapid and the binding more specific to the tumor than for whole native immunoglobulin, subtraction techniques can be dispensed with or modified for use in particular circumstances. In addition, the use of labeled antibody fragments for a more direct intra-arterial application of a labeled detection agent to the tumor supplied by the particular artery presents an important opportunity of this process, both for tumor detection and for tumor radiotherapy.

Because antibody fragments are diffused into the tissues much more rapidly and more rapidly localized, tumor detection and localization may be achieved within a short time of injection of the labeled fragments. This is a decided advantage over known procedures, which usually permit tumor localization only after about 24 hours following administration of the labeled whole antibodies.

Mixtures of labeled antibody fragments may be used in a single preparation for tumor localization, detection or therapy. Fragments of different size may be used together. The mixture can use antibodies specific to antigens associated with the same tumor type to enhance localization and resolution. Alternatively, broad screening for various tumor types can be done using a mixture of antibodies with diverse tumor specificities.

Antibody fragments may be labeled by any of several techniques known to the art. A wide range of labeling techniques are disclosed in Feteanu, "Labeled Antibodies in Biology and Medicine", pages 214–309 (McGraw-Hill Int. Book Co., New York et al, 1978). The introduction of various metal radioisotopes may be accomplished according to the procedures of Wagner et al., *J. Nucl. Med.*, 20, 428 (1979); Sundberg et al, *J. Med. Chem.*, 17, 1304 (1974); and Saha et al, *J. Nucl. Med.*, 6, 542 (1976). The foregoing are merely illustrative of the many methods of radiolabeling proteins known to the art.

Among the radioisotopes used, gamma-emitters, positron-emitters, x-ray-emitters and fluorescence-emitters are suitable for localization and/or therapy, while beta-emitters and alpha-emitters may also be used for therapy. Suitable radioisotopes for labeling antibodies include Iodine-131, Iodine-123, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m and Fluorine-18. The halogens can be used more or less interchangeably as labels since halogen-labeled antibody fragments and/or normal immunoglobulin fragments would have substantially the same kinetics and distribution and similar metabolism.

A preferred labeling technique involves labeling with either Iodine-131 (I-131) or Iodine-123 (I-123) using an oxidative procedure wherein a mixture of radioactive potassium or sodium iodide and the antibody is treated with chloramine-T, e.g., as reported by Greenwood et al, *Biochem. J.*, 89, 114 (1963) and modified by McCohahey et al, *Int. Arch. Allergy Appln. Immunol.*, 29, 185 (1969). This results in direct substitution of iodine atoms for hydrogen atoms on the atibody molecule, presumably on tyrosine residues, possibly also on tryptophane and even on phenylalanine residues, depending on the proportions of reagents and the reaction conditions. Alternatively, lactoperoxidase iodination may be used, as described in Feteanu, supra, page 303 and references cited therein.

In general, it is desirable to introduce as high a proportion of radiolabel as possible into the antibody fragment without destroying its immunospecificity. While the vast majority of investigators had considered that introduction by direct substition of more than from 1.5 to 2 iodine atoms per intact antibody is disadvantageous, it has now been found that, especially where the fragment is highly marker-specific prior to labeling, even a reduction of the antibody fragment specificity of from 5 to 33% as a consequence of high labeling is outweighed by the advantage of high activity, permitting the use of substantially smaller quantities of labeled fragment. As noted above, the use of highly specific antibody fragments of high activity results in efficient localization and increased resolution. This balancing of increased activity with reduced specificity is advantageous with up to an average of about 10 atoms of iodine per antibody fragment after which the reduction in specificity outweighs the advantage of high activity. Using other methods for the introduction of radiolabel, it may be possible to further increase the proportion of label to antibody fragment without paying an unacceptable price in reduced immunospecificity. A further improvement may be achieved by effecting radiolabeling in the presence of the specific antigen, to insure that the antigen binding site on the antibody will be protected. The antigen is separated after labeling.

A further aspect of the present invention relates to the use of antibody fragments containing both a radioisotope label and an addend containing significant numbers of boron atoms, including at least the normal 20% distribution of boron-10 isotope. The boron-containing addend may be introduced by a variety of methods, preferably by coupling the antibody fragment with a boron-rich coupling agent, such as the diazonium ion derived from 1-(4-aminophenyl)-1,2-dicarba-closo-dodecarborane(12), according to the method of Hawthorne et al., *J. Med. Chem.*, 15, 449 (1972). The boron-10-containing antibody fragment is then radiolabeled according to one or more of the above procedures to produce a fragment containing both one or more radiolabels for tumor localization and/or therapy and a high content of boron-10 atoms for the absorption of thermal neutrons. Boron-10 absorbs thermal neutrons and the activated nucleus decays rapidly to Lithium-7 and an alpha-particle. These resultant alpha-particles are cytotoxic, and their production in tumor cells kills the cells and causes tumor reduction.

Combination of a boron addend with one or more radiolabels on a highly marker-specific antibody fragment provides for the first time a single agent which functions as a multimodal tumor therapeutic agent. The rapid and specific localization of these doubly labeled antibody fragments at the site of a tumor permits a rapid and precise definition of the areas where neutron irradiation should be focused. Moreover, as tumor cells are destroyed by the combined effects of radiation from the radiolabel and neutron-activated boron-10 emissions, and the killed tumor cells are eliminated, the progress of the radiotherapeutic treatment may be monitored by measurement of localized, radio labeled antibody fragments, or other tumor detection methods.

Examples of bivalent hybrid antibody fragments, e.g., F(ab')$_2$ antibody fragments obtained by chemical combination of Fab' fragments from each of two different tumor-specific antibodies are shown below. Table 1 gives an illustrative list of suitable such bivalent hybrids and tumor types for which they are advantageously used, both for detection and therapy. The first column shows the two antigens to which the two Fab' components of the hybrid are specific, each hybrid having one fragment specific to an antigenic determinant of each.

In some cases, the antibody will be raised to a smaller fragment of a tumor-associated antigen to increase the specificity. For example, antibodies raised against the beta-subunit of HCG are preferred over antigens raised against HCG itself. The second column shows tumor types which preferentially concentrate each hybrid type.

TABLE 1

F(ab')₂ Hybrid Antibody Fragments and Associated Tumor Types

| Components | Tumors |
|---|---|
| AFP/HCG | Germ cell, trophoblastic, testicular, ovarian, gastrointestinal |
| CEA/CSAp | Gastrointestinal, e.g., colon, rectal, stomach, pancreatic |
| CEA/POA | Pancreatic, lung |
| CEA/HCG | Lung, ovarian, gastrointestinal |
| CEA/AFP | Liver, gastrointestinal, ovarian, testicular |
| CEA/TPA | Most |
| CEA/ferritin | Solid, hematopoietic, liver |
| CEA/calcitonin | Thyroid |
| CEA/PAP | Prostatic |
| CEA/Parathormone | Parathyroid, lung |
| HCG/PBG | Trophoblastic |
| CGA/GEA | Brain |
| GFA/CMA | Brain |

Legend:
CEA—Carcinoembryonic antigen
HCG—Human chorionic gonadotropin (or beta-subunit)
CSAp—Colon specific antigen-p
POA—Pancreatic oncofetal antigen
AFP—Alpha-fetoprotein
TPA—Tissue polypeptide antigen
PAP—Prostatic acid phosphatase
PBG—Pregnancy beta₁-globulin
CGA—Common glioma antigen
GEA—Glioembryonic antigen
GFA—Glial fibrillary acidic protein
CMA—Common meningioma antigen Hybrid fragments such as those shown in Table 1 may be labeled with a single radioisotope for the detection and localization of multiple tumor types or cells, or labeled with one or more radioisotopes for therapy. Furthermore, such hybrids may be labeled with a radioisotope for detection and one or more isotopes for therapy, e.g., a radioisotope and/or a boron-containing fragment so that the localized tumor may then be irradiated with thermal neutrons in the manner disclosed above.

Radioactivity due to accumulation of labeled antibody fragments or their metabolites in the blood-pool or in interstitial fluids can significantly reduce the resolution of tumor localization using labeled antibody fragments specific to tumor-associated markers. In such cases, it is advantageous to inject a reference substance into the subject prior to photoscanning, the reference substance being radiolabeled with a radioisotope emitting at a different energy from the marker specific antibody fragment label and capable of independent detection by the photoscanning device. The level of activity of the reference substance is used to determine the background activity due to non-targeted specific antibody fragment, this background activity is then subtracted from the total activity of the specific antibody permitting a determination of the activity of substantially only the targeted, tumor-associated antibody.

It is know to use technetium-99m-labeled substances for a determination of blood pool and interstitial background activity, as disclosed in Goldenberg et al, New Eng. J. Med., 298, 1348 (1978). That reference discloses the use of Tc-99m-labled human serum and Tc-99m-pertechnetate. Separate injection of these reference substances was necessary prior to each photoscan.

The present invention includes the use of Tc-99m-labeled normal immunoglobulin G or fragments thereof and Tc-99m-labeled sulfur colloid among suitable reference substances. Preferably, however, the reference substance is the corresponding normal, indifferent immunoglobulin G fragment from the same or different species as that used to prepare the specific antibody fragment used as the tumor localization agent. This normal immunoglobulin G fragment is preferably radiolabeled with a different isotope of the same element used to label the specific antibody fragment, and is preferably injected concurrently with the radiolabeled marker-specific fragment. This has the advantage of using as a reference substance a molecular species having essentially the same kinetics of binding, distribution and metabolism as the labeled specific fragment. As a consequence, only a single injection of the reference substance is necessary, and increased resolution is achieved. The normal IgG fragments are prepared and labeled in the same way as the specific fragments to which they correspond.

Suitable such pairs of radioisotopes, one of which may be used for labeling the specific antibody fragment and the other of which is used to lable the normal immunoglobulin include Iodine-131 and Iodine-123; Indium-111 and Indium-113m; Gallium-67 and Gallium-68; Ruthenium-97 and Ruthenium-103; or Mercury-197 and Mercury-203. Because iodine may be introduced directly by a chemical substitution reaction, and has at least five isotopes which are radioactive and detectable using a photoscanning device, iodine is preferred for radiolabeling both the specific antibody fragment and the normal immunoglobulin G reference fragment for use in the method of the invention. Advantageously, Iodine-131 is used for labeling the specific fragment and Iodine-123 is used for labeling the normal immunoglobulin fragment. The resultant emissions are separately detectable on two different channels of a gamma-scintillation detector.

The resultant scanning data are conveniently stored in a minicomputer and the aforementioned subtraction procedure is effected to determine the regions of excess accumulation of radiolabeled specific fragment over its ratio to labeled reference immunoglobulin fragment in non-target areas. These values may be used to generate a related output signal, advantageously a gradation of colors on a color television screen. The photoscanning device may also include computed tomographic capabilities. The combination of this highly efficient subtraction technique with the use of highly monospecific, preferably monoclonal antibody fragments labeled to give the maximum balance between high activity and acceptable immunospecificity provides a tumor localization and detection method of significantly improved resolution.

The antibody fragments of the invention are advantageously administered in the form of injectable compositions. For general screening and for many types of localization and therapy, injection will be intravenous or intra-arterial. The injectable antibody fragment solution will be dripped into a vein or artery over the course of from 5 minutes to about 45 minutes, preferably from 10 minutes to 20 minutes. In certain cases, intradermal, intracavitary or intrathecal administration is advantageous. Where the tumor is supplied by a known artery, intra-arterial administration is preferred for therapy. In addition, either intrathecal administration or injection into the carotid artery are advantageous for therapy of tumors located in the brain. Intracavitary administration is advantageous for tumors that are spread in particular body cavities.

A typical injectable composition according to the invention contains about 10 mg human serum albumin (1%, USP:Park-Davis) and from 25 to 200 micrograms of radiolabeled specific antibody fragment per milliliter of 0.01 M phosphate buffer (pH 7.5: Bioware) containing 0.9% NaCl. Where the subtraction technique of the invention is used, a quantity of radiolabeled normal immunoglobulin fragment roughly equal to the weight of specific antibody fragment is also included. Other conventional pharmaceutically acceptable injection vehicles may be used where indicated, such as for intrathecal or intracavitary injection.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Antibodies used in these examples are highly specific, either prepared by conventional immunization followed by complement inactivation, adsorption to remove hemagglutination components and affinity purification against cross-reactive antigens and the specific antigen, or hybridoma-derived monoclonal antibodies. Details of preparation of representative antibodies are disclosed in copending applications of the present inventor, Ser. No. 126,262, filed Mar. 3, 1980, to M. D. Goldenberg, entitled Tumor Localization and Therapy With Labeled Anti-CEA Antibody, and Ser. No. 126,261, Mar. 3, 1980, to M. D. Goldenberg, entitled Tumor Localization and Therapy With Labeled Antibodies Specific to Intracellular Tumor-Associated Markers. The disclosures of these two copending applications are incorporated by reference in this application.

EXAMPLE 1

Preparation and Labeling of antibody F(ab')$_2$ and Fab' Fragments (a) Affinity purified goat anti-CEA IgG, 2 ml of 15 mg/ml in phosphate buffered saline, is dialyzed against 1 liter of sodium acetate buffer, 100 mM, pH 4.0 (NaAc) for 24 hours at 4° C. The antibody solution is transferred to a screw top tube, preheated to 37° C. and incubated with hog pepsin (Sigma), 0.1 ml of 3 mg/ml in NaAc, for 16 hours at 37° C. The digest, including any precipitate, is dialyzed against sodium phosphate buffer, 100 mM, pH 7.5 (PO$_4$) for 6 hours at 4° C. The resultant solution is chromatographed on Sephadex G-100 with PO$_4$, the F(ab')$_2$ fragments eluting in the second protein peak. The F(ab')$_2$ fractions are combined, concentrated by ultrafiltration and dialyzed against PO$_4$, 50 mM, pH 7.5, and stored at −20° C.

(b) The resultant solution of part (a) prior to gel filtration chromatography is treated with $\beta$-mercaptoethanol, 7 $\mu$l per ml of sample, and incubated for 0.5 hour at 4° C. with constant stirring. Iodoacetamide, 1 M, 0.135 ml per ml of sample, is added and the mixture incubated for 1 hour at 4° C. with stirring, followed by clarification by centrifugation.

The resultant solution of crude Fab' fragments is purified by gel filtration on Sephadex G-100, and anti-CEA Fab' fragments eluting in the second protein peak. The fractions of peak two are pooled, concentrated by ultrafiltration, dialyzed against PO$_4$, 50 mM, pH 7.5, and stored at −20° C.

(c) By the procedure of part (a), F(ab')$_2$ fragments of anti-HCG, anti-AFP anti-CSAp, anti-CGA, anti-GEA, anti-GFA, anti-CMA and anti-HAAA are prepared.

(d) By the procedures of parts (a) and (b), the Fab' fragments of anti-HCG, anti-AFP, anti-CSAp, anti-CGA, anti-GEA, anti-GFA, anti-CMA and anti-HAAA are prepared.

(c) 10 $\mu$g IgG per mCi $^{131}$I, is injected into a radionuclide vial containing $^{131}$I (Amersham-Searle).

Chloramine-T and sodium metabisulfite solutions are prepared by the injection of 5 ml of sterile pyrogen-free 0.5 M pH 7.5 phosphate buffer into each of two vials containing 10 mg of chloramine-T and 50 mg of bisulfite, respectively. Chloramine-T solution is injected, 10 $\mu$g/mCi $^{131}$I, into the rationuclide vial. Sodium metabisulfite solution, 5 times the amount of chloramine-T, is injected into the vial exactly 90 seconds after the chloramine-T. The mixture is removed from the reaction vial with a sterile syringe, the reaction vial is rinsed twice with 1% normal human serum albumin, and the rinses combined with the reaction mixture.

The sample of $^{131}$I-antibody F(ab')$_2$ is applied to a PD-10 Sephadex G-25 column which is pre-equilibrated with 1% normal human serum albumin in PBS, eluted with approximately 4.5 ml of 1% normal human serum albumin in PBS, monitored with a shielded gamma detector (Eberline), collected and diluted to a predetermined concentration for storage and use.

The resultant $^{131}$I-antibody F(ab')$_2$ has an average of from 3 to 7 atoms of iodine per fragment. Random aliquots from each batch are separately tested for sterility, pyrogenicity, toxicity and other quality control variables.

EXAMPLE 2

Preparation and labeling of hybrid fragments (a) A mixture of equal quantities of anti-CEA and anti-CSAp F(ab')$_2$ fragments prepared in Example 1(c), in the form of 15 mg/ml solutions in pH 5.0 NaAc buffer, is treated with a solution of 0.01 M $\beta$-mercaptoethylamine hydrochloride, 7 $\mu$l per ml of sample and incubated for 1 hour at 37° C. with constant stirring. The mixture is passed through an ion exchange column (IR 120) at pH 5 and 40° C. to remove the reducing agent, the resultant solution adjusted to pH 8 and stirred for 2 hours with gentle stirring and passage of oxygen through the solution. The solution is then dialyzed against PO$_4$ for 6 hours at 4° C. and chromatographed on Sephadex G-100 with PO$_4$ as in final step of Example 1(a).

The fraction containing F(ab')$_2$ hybrids elutes in the second protein peak. This fraction is subjected to affinity chromatography on separate Sepharose 4B columns with cyanogenbromide linked CEA and CSAp. That fraction retained by both columns is chaotropically dissociated, re-chromatographed on Sephadex G-100 and further purified by precipitation with sodium sulfate, dissolution and dialysis against PO$_4$, and the solution of anit-CEA/CSAp F(ab')$_2$ is stored at −20° C.

(b) By the procedure of part (a), the following hybrid F(ab')$_2$ fragments are prepared, the component Fab' amines being indicated by their antibody source:

(i) AFP/HCG F(ab')$_2$ (ii) CEA/PAP F(ab')$_2$
(iii) CFA/GEA F(ab')$_2$ (c) The fragments prepared in parts (a) and (b) are each radiolabeled with either I-131 or I-133 by the procedure of Example 1(e).

EXAMPLE 3

Preparation and labeling of normal IgG Fragments

Normal goat immunoglobulin G (IgG) (Miles) is affinity purified against cyanogen bromide-linked HCG, AFP, CSAp, CEA, PAP, GEA and CFA, fragmented by the procedures of Example 1, and the fragments radiolabeled with I-123 as in Example 1(e), except that I-123 is substituted for I-131 with proportional changes in the reagents to account for differences in specific activity.

EXAMPLE 4

Preparation and labeling of Boron-10-containing antibody Fragments (a) An antibody fragment, e.g., anti-CEA F(ab')$_2$ prepared according to Example 1, is reacted with a 20-fold molar excess of the diazonium salt of 1-(4-aminophenyl)-1,2-dicarba-closododecaborane(12) having a natural abundance of Boron-10 isotrope (20%), using the procedure of Hawthorne et al., *J. Med. Chem.*, 15, 449 (1972). The resultant fragment has an average of from 2 to 10 diazo-linked carborane residues or from 4 to 20 Boron-10 atoms per antibody fragment.

(b) The anti-CEA-$^{10}$B-F(ab')$_2$ of part (a) is radiolabeled with I-131 as in Example 1(e), to introduce an average of from 2.5 to 10 atoms of iodine per antibody fragment.

(c) The F(ab')$_2$ fragments of Example 1(c) are each reacted to add a carborane addend according to the procedure of part (a) of this example, and the resultant Boron-10-containing fragments are radioiodinated by the procedure of Example 1(e).

(d) The procedure of Example 1(b) is followed, except that the N-iodoacetamide of 1-(4-aminophenyl)-1,2-dicarba-closododecaborane(12) is used in place of iodoacetamide. The amide is prepared by reacting the amine with iodoacetyl chloride in the presence of base, according to conventional procedures. The resultant Fab' fragments bear two carboranophenyl-substituted acetamide groups on the sulfhydryl groups liberated in the reductive cleavage. The Boron-10-containing fragments are radioiodinated according to the procedure of Example 1(c).

(e) The hybrid F(ab')$_2$ fragments prepared according to Example 2(a) and 2(b) are reacted as in part (a) of this example and then radioiodinated according to the procedure of Example 1(e).

EXAMPLE 5

Preparation of Injectable Compositions

Sterile, pyrogen-free solutions are prepared as shown.

(a) A sterile solution containing, per ml:
(1) 10 mg Human Serum Albumin (HSA) (1%, USP, Parke-Davis)
(2) 0.01 M phosphate buffer, pH 7.5 (Bioware)
(3) 0.9% NaCl
(4) 80 μg $^{131}$I-anti-CEA F(ab')$_2$ (goat) prepared according to Example 1 (average of about 5 atoms of iodine/molecule, specific activity of about 40 μCi/μg).

The labeled antibody of Example 1 is stored in a solution of (1), (2) and (3) at a concentration of 320 μg/ml and diluted with three volumes of 1% HSA in phosphate buffered saline (PBS) to prepare this solution.

(b) A sterile solution according to the procedure of part (a) except that it further contains 80 μg/ml of $^{123}$I-F(ab')$_2$ as prepared in Example 3. The $^{123}$I-F(ab')$_2$ is stored in phosphatebuffered saline containing 1% HSA at a concentration of 320 μg/ml. An equal volume of this solution is used in place of one volume of 1% HSA in PBS in the procedure of part (a).

(c) A sterile solution according to the procedure of part (b) except that the antibody is 40 μg/ml of the $^{131}$I-anti AFP Fab' prepared according to Example 1, stored in 1% HSA in PBS at a concentration of 160 μg/ml, (average of 2.5 atoms of iodine per fragment), having about half the activity of the $^{131}$I-anti-CEA F(ab')$_2$ fragment, and with $^{123}$I-Fab' instead of $^{123}$I-F(ab')$_2$ at equal activity to the antibody fragment.

(d) A sterile solution according to the procedure of part (b) except that the antibody is the $^{131}$I-anti-CSAp F(ab')$_2$ prepared according to Example 1, stored in 1% HSA in PBS at a concentration of 320 μg/ml and having comparable activity.

(e) A sterile solution according to the procedure of part (b) except that the antibody is the $^{131}$I-anti-CEA/CSAp hybrid F(ab')$_2$ prepared according to Example 2, stored in 1% HSA in PBS at a concentration of 320 μg/ml and having comparable activity.

(f) A sterile solution according to the procedure of part (b) except that it further contains $^{131}$I-anti-AFP F(ab')$_2$ and $^{131}$I-anti-HCG F(ab')$_2$, 80 μg/ml each, stored in 1% HSA in PBS at concentrations of 320 μg/ml each, and having comparable activity, an equal volume of each being used in place of one volume of 1% HSA in PBS in the procedure of part (a).

(g) A sterile solution according to the procedure of part (e) except that it further contains the $^{133}$I-anti-AFP/HCG F(ab')$_2$ hybrid prepared according to Example 2, stored in 1% HSA in PBS at a concentration of 320 μg/ml and having comparable activity.

(h) A sterile solution according to the procedure of part (b) except that the antibody is the $^{131}$I-anti-CGA/GEA F(ab')$_2$ fragment prepared according to Example 2, stored in 1% HSA in PBS at a concentration of 320 μg/ml and having comparable activity.

(i) A sterile solution according to the procedure of part (b) except that the antibody is $^{131}$I-anti-CEA-$^{10}$B F(ab')$_2$ fragment prepared according to Example 4, having an average of 5 diazo-linked carborane residues and 3 atoms of iodine per antibody molecule, and a specific activity of about 48 μCi/μg. The final solution contains 133 μg/ml of the antibody.

(j) A sterile solution according to the procedure of part (b) except that the antibody is the $^{131}$I-anti-CEA/CSAp-$^{10}$B hybrid F(ab')$_2$ prepared according to Example 4, having an average of 5 diazo-linked carborane residues and 3 atoms of iodine per antibody molecule, and a specific activity of about 48 μCi/μg. The final solution contains 133 μg/ml of the antibody.

(k) A sterile solution according to the procedure of part (b) except that the antibody is the $^{131}$I-anti-AFP-$^{10}$B Fab' fragment prepared according to Example (d) having an average of 5 diazo-linked carborane residues and 3 atoms of iodine per antibody molecule, and a specific activity of about 48 µCi/µg. The final solution contains 63 µg/ml of the antibody.

(l) A sterile solution according to the procedure of part (b) except that the antibody is the $^{131}$I-anti-CGA/-GEA-$^{10}$B hybrid F(ab')$_2$ fragment prepared according to Example 4, having an average of 5 diazo-linked carborane residues and 3 atoms of iodine per antibody molecule, and a specific activity of about 48 µCi/µg. The final solution contains 133 µg/ml of the antibody.

EXAMPLE 6

Tumor Localization

Radioiodinated antibody fragment is administered to patients with suspected tumors. The patient is pretreated for anaphylactic hypersensitivity to the corresponding IgG fragment. To block thyroid uptake of I-131 or I-123, Lugol's solution (Purepack) is administered by mouth, 5 drops twice daily for seven days beginning one day before injection of the radioactively labeled antibody.

(a) Localization is effected according to the procedure of Goldenberg et al., *N. Eng. J. Med.*, 298, 1384 (1978), by infusion of 0.06 ml of a solution of $^{131}$I-anti-CEA F(ab')$_2$ containing $^{123}$I-F(ab')$_2$ prepared according to Example 5(b) in 20 ml of sterile physiological saline over a period of from 10 minutes to 20 minutes. No Tc-99m compounds are used, the subtraction technique being adapted in a conventional fashion to discriminate between I-131 and I-123. Scans are taken immediately and at 2, 4, 8, 12, 24, 48 and 72 hours after injection of the fragment is completed.

Data analysis involves storing the photoscanning data in a computer, equalizing the activity level of the labeled normal IgG fragment with that of the labeled specific fragment in at least one non-target area and calculating a background level value for the labeled fragment for each data point; subtracting the resultant background value from the total fragment activity, pixel-by-pixel, to generate a value for the activity of targeted fragment for each data point; and using the resultant generated values for targeted fragment activity to generate a related output signal.

Significant localization is seen after 2 hours, with improved resolution with time, tending to plateau between 4 and 12 hours after injection. No additional background $^{123}$I-F(ab')$_2$ is added. The CEA-selectivity of this method is comparable to the earlier Goldenberg et al method, but the resolution, rapidity and convenience are enhanced significantly.

(b) The procedure of part (a) is followed using 0.06 ml of the solution of Example 5(c) instead of the solution of Example 5(b).

Imaging is comparable to that in part (a), being especially successful in patients with testicular and hepatic cancers. Secondary lung and abdominal metastases are well localized despite serum AFP levels which are often highly elevated.

(c) The procedure of part (a) is followed using 0.06 ml of the solution of Example 5(d) instead of the solution of Example 5(b).

Imaging is comparable to that in part (a), being especially successful in patients with colon cancers.

(d) The procedure of part (a) is followed using 0.06 ml of the solution of Example 5(e) instead of the solution of Example 5(b).

Imaging of gastrointestinal cancers is especially sharp, even compared to parts (a) and (c) of this Example.

(e) The procedure of part (a) is followed using 0.06 ml of the solution of Example 5(f) instead of the solution of Example 5(b).

Imaging of all tumors of the types successfully localized and detected in parts (a), (b) and (c) of this Example is successful. The combination scan gives enhanced localization and resolution in many cases, especially embryonal, germ cell, liver and lung cancers.

(f) The procedure of part (a) is followed using 0.06 ml of the solution of Example 5(g) instead of the solution of Example 5(b).

Imaging is comparable to that in part (d) of this Example for all tumor types imaged by the procedures of parts (a)-(d) of this Example.

(g) The procedure of part (a) is followed using 0.06 ml of the solution of Example 5(h) instead of the solution of Example 5(b).

Imaging of a glioblastoma of the brain is successful, showing that the hybrid antibody can pass through the blood-brain barrier and localize in a brain tumor.

EXAMPLE 7

Tumor Therapy (a) A patient having an ovarian cancer, optionally detected and localized by the procedure of Example 6, is injected by intravenous infusion with 150 mCi of the solution of Example 5(a) in 50 ml of sterile physiological saline. Reduction in tumor size is observed within 20 days. The dose is repeated at intervals adjusted on an individual basis.

(b) A patient having a cervical cancer optionally detected and localized by the procedure of Example 6, is injected with an amount of the solution of Example 5(i) (in 50 ml of sterile physiological saline) sufficient to provide 200 µCi of $^{131}$I activity based on a 70 kg patient weight.

The tumor is precisely localized 12 hours after injection using the procedure of Example 6. A well collimated beam of thermal neutrons is focused on the defined tumor locations. Irradiation with an external neutron beam dose of 400-800 rads, delivered in a period of from 8-20 min, is effected for each tumor locus, and is optionally repeated with administration of the tumor-localizing antibody, with or without the radiolabel, at intervals adjusted on an individual basis, but usually not exceeding a total dose of 3200 rads unless simultaneous external neutron beam therapy is indicated.

(c) The procedure of part (b) is repeated except that the solution of Example 5(j) is used instead of the the solution of Example 5(i), and the patient has a colon cancer. Successful tumor reduction is observed.

(d) The procedure of part (b) is repeated except that the solution of Example 5(k) is used instead of the solution of Example 5(i), and the patient has a germ-cell tumor of the testis. Successful tumor reduction is observed, including reduction of abdominal metastases.

(e) The procedure of part (b) is repeated except that the solution of Example 5(l) is used instead of the solution of Example 5(i), and the patient has a glioblastoma of the brain. Successful tumor reduction is observed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for detecting and localizing a tumor which either produces or is associated with a cytoplasmic, intracellular or cell-surface marker substance which comprises injecting a human subject parenterally with a marker-specific fragment obtained by cleavage of an antibody specific to said marker substance and radiolabeled with a pharmacologically inert radioisotope capable of detection using a photoscanning device, and subsequently scanning with said device to detect and locate the site or sites of uptake of said labeled antibody fragment by said tumor.

2. The method of claim 1, wherein said market substance is an oncofetal antigen.

3. The method of claim 1, wherein said market substance is a placental antigen.

4. The method of claim 1, wherein said marker substance is an oncogenic or tumor or tumor virus-associated antigen.

5. The method of claim 1, wherein said marker substance is a tissue- or organ-associated antigen, an ectopic hormone or a normal antigen or variant thereof.

6. The method of claim 1, wherein said marker substance is carcinoembryonic antigen (CEA).

7. The method of claim 1, wherein said marker substance is alphafetoprotein (AFP).

8. The method of claim 1, wherein said marker substance is human chorionic gonadotropin (HCG) or the beta-subunit thereof.

9. The method of claim 1, wherein said marker substance is colon-specific antigen-p (CSAp).

10. The method of claim 1, wherein said market substance is one of prostatic acid phosphatase, pancreatic oncofetal antigen, placental alkaline phosphatase, pregnancy beta$_1$-globulin, parathormone, calcitonin, tissue polypeptide antigen, T-antigen, beta$_2$-microglobulin, mammary tumor-associated glycoproteins (MTGP), galactosyl transferase-II (GT-II), gp-52 viral-associated antigen, ovarian cystadenocarcinoma-associated antigen (CA-58, CCA, TA-4), basic fetoprotein (BFP), terminal deoxynucleotidyl transferase (TdT), cytoplasmic melanoma-associated antigens, human astrocytoma-associated antigen (HAAA), common glioma antigen (CGA), glioembryonic antigen (GEA), glial fibrillary acidic protein (GFA), common meningioma antigen (CMA), ferritin, and tumor angiogenesis factor (TAF).

11. The method of claim 1, wherein said marker-specific fragment is an Fab, Fab', and F(ab')$_2$ fragment obtained by cleavage of said specific antibody.

12. The method of claim 1, wherein said radioisotope is one of Iodine-131, Iodine-123, Iodine-126, Iodine-133, Bromine-77, Indium-111, Indium-113m, Gallium-67, Gallium-68, Ruthenium 95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m and Fluorine-18.

13. The method of claim 1, wherein said radioisotope is Iodine-131 or Iodine-123.

14. The method of claim 1, wherein the amount of radiolabel introduced by direct chemical substitution into said marker-specific antibody fragment is sufficient to reduce its specific market substance immunoreactivity by from 5 to 33%.

15. The method of claim 1, wherein said marker-specific antibody fragment is substantially monospecific for the marker substance, having a crossreactivity with other antigens of less than 15% and an immunoreactivity for the marker substance of more than 50%.

16. The method of claim 1, wherein the specific antibody cleaved to produce said marker-specific fragment is a monoclonal antibody having a marker substance specificity of at least 90%.

17. The method of claim 1, wherein said fragment is labeled with a radioisotope of iodine, an average of at least 2.5 atoms of iodine per fragment molecule being introduced and no more than will reduce the antibody specificity by more than 33%.

18. The method of claim 1, wherein said tumor is located in the brain and said fragment is injected intravenously, intraarterially or intrathecally.

19. The method of claim 18, wherein the fragment is injected intravenously.

20. The method of claim 1, wherein prior to photoscanning, a second substance is injected into the subject, said second substance being radiolabeled with a radioisotope emitting at a different energy from the antibody fragment label and capable of independent detection by said photoscanning device, the level of activity of said second substance being used to determine the background activity due to non-targeted specific antibody fragment, said background activity being subtracted from the total activity of the specific antibody fragment, whereby the activity of substantially only the targeted, tumor-associated antibody fragment is determined.

21. The method of claim 20, wherein said second substance is technetium-99m-labeled normal human immunoglobulin, technetium-99m-labeled human serum, technetium-99m-sulfur colloid, technetium-99m-pertechnetate, or a combination thereof.

22. The method of claim 20, wherein said second substance is the corresponding fragment obtained by analogous cleavage of normal immunoglobulin from the same or different species as that used to prepare said specific antibody.

23. The method of claim 22, wherein said corresponding fragment is labeled with a different isotope of the same element used to label the fragment of said specific antibody.

24. The method of claim 23, wherein the specific antibody fragment is labeled with one of a pair of radioisotopes, and the corresponding normal immunoglobulin fragment is labeled with the other of the pair, said pair being Iodine-131 and Iodine-123; Indium-111 and Indium-113m; Gallium-67 and Gallium-68; Ruthenium-97 and Ruthenium-103; or Mercury-197 and Mercury-203.

25. A method for detecting and localizing a tumor which either produces or is associated with a cytoplasmic, intracellular or cell-surface marker substance, which comprises injecting a human subject parenterally with two marker-specific fragments, one fragment being a marker-specific fragment obtained by cleavage of a first antibody specific to a first tumor associated marker and the second fragment being a marker-specific fragment obtained by cleavage of a second antibody specific to a second, different tumor-associated marker, each of said fragments being radiolabeled with a pharmacologically inert radioisotope capable of detection using a photoscanning device, and subsequently scanning with said device to detect and locate the site or sites of uptake of one or both of said labeled fragments by said tumor.

26. The method of claim 25, wherein said two marker-specific fragments are obtained by cleavage of two of anti-CEA antibody, anti-AFP antibody, anti-HCG antibody and anti-CSAp antibody.

27. The method of claim 26, wherein said two fragments are labeled with different radioisotopes.

28. The method of claim 25, wherein prior to photoscanning, a reference substance is injected into the subject, said reference substance being radiolabeled with a radioisotope emitting at a different energy from either antibody fragment label and capable of independent detection by said photoscanning device, the level of activity of said reference substance being used to determine the background activity due to non-targeted specific antibody fragment, said background activity being subtracted from the total activity of each specific antibody fragment, whereby the activity of substantially only targeted, tumor-associated antibody fragments is determined.

29. The method of claim 28, wherein said reference substance is technetium-99m-labeled normal human immunoglobulin, technetium-99m-labeled human serum, technetium-99m-sulfur colloid, technetium-99m-pertechnetate, or a combination thereof.

30. The method of claim 28, wherein each of said two fragments is labeled with a different radioisotope; a fragment obtained by analogous cleavage of normal immunoglobulin from the same or different species used to prepare each said specific antibody and corresponding to each of said two fragments is used as a reference substance; each said reference fragment is labeled with a different isotope of the same element used to label the corresponding fragment of said specific antibody; and the activity of the reference fragment corresponding to each of said two fragments is used to determine the background activity and the targeted fragment activity for the specific antibody fragment to which it corresponds.

31. A method for detecting and localizing a tumor which either produces or is associated with a cytoplasmic, intracellular or cell-surface marker substance, which comprises injecting a human subject parenterally with an F(ab')$_2$ hybrid formed from two chemically joined Fab' fragments, said fragments being a first marker-specific Fab' fragment obtained by cleavage of an antibody specific to a first tumor-associated marker and a second, different marker-specific Fab' fragment obtained by cleavage of a second antibody specific to the same or different tumor-associated marker, said hybrid being radiolabeled with a pharmacologically inert radioisotope capable of detection using a photoscanning device, and subsequently scanning with said device to detect and locate the site or sites of uptake of said labeled hybrid by said tumor.

32. The method of claim 31, wherein said hybrid is obtained by cleavage and recombination of a mixture of F(ab')$_2$ fragments specific to each said specific antibody.

33. The method of claim 31, wherein said hybrid contains a marker-specific Fab' arm obtained by cleavage of anti-CEA antibody, anti-AFP antibody, anti-HCG antibody, or and anti-CSAp antibody.

34. The method of claim 31, wherein said hybrid contains marker-specific Fab' arms obtained by cleavage of two different antibodies selected from anti-CEA antibody, anti-AFP antibody, anti-HCG antibody and anti-CSAp antibody.

35. The method of claim 31, wherein prior to photoscanning, a second substance is injected into the subject, said second substance being radiolabeled with a radioisotope emitting at a different energy from the hybrid label and capable of independent detection by said photoscanning device, the level of activity of said second substance being used to determine the background activity due to non-targeted hybrid, said background activity being subtracted from the total activity of the hybrid, whereby the activity of substantially only the targeted, tumor-associated hybrid is determined.

36. The method of claim 35, wherein said second substance is technetium-99m-labeled normal human immunoglobulin, technetium-99m-labeled human serum, technetium-99m-sulfur colloid, technetium-99m-pertechnetate, or a combination thereof.

37. The method of claim 35, wherein said second substance is an F(ab')$_2$ fragment obtained by analogous cleavage of normal immunoglobulin from the same or different species as that used to prepare either said antibody specific to a first tumor-associated marker or said second antibody specific to the same or different tumor-associated marker.

38. The method of claim 37, wherein said second substance is labeled with a different isotope of the same element used to label the F(ab')$_2$ hybrid.

39. The method of claim 38, wherein the F(ab')$_2$ hybrid is labeled with Iodine-131 or Iodine-123 and the second substance is labeled with the other of Iodine-131 or Iodine-123.

40. A method of tumor radiotherapy, which comprises parenterally injecting into a human subject having a tumor which produces or is associated with a cytoplasmic, intracellular or cell-surface marker substance an effective tumor reducing amount of a marker-specific fragment obtained by cleavage of an antibody specific to said marker substance and radiolabeled with a pharmaceutically inert, radiotherapeutically effective radioisotope.

41. A method of tumor radiotherapy, which comprises parenterally injecting into a human subject having a tumor which either produces or is associated with at least one cytoplasmic, intracellular or cell-surface marker substance an effective tumor reducing amount of an F(ab')$_2$ hybrid formed from two chemically joined Fab' fragments, said fragments being a first marker-specific Fab' fragment obtained by cleavage of an antibody specific to a first tumor-associated marker and a second, different marker-specific Fab' fragment obtained by cleavage of a second antibody specific to the same or different tumor-associated marker, said hybrid being radiolabeled with a pharmacologically inert, radiotherapeutically effective radioisotope.

42. The method of claim 41, wherein said F(ab')$_2$ hybrid is prepared by the steps of pepsin-catalyzed cleavage of anti-CEA antibody to produce an F(ab')$_2$ fragment and reductive cleavage thereof to form CEA-specific Fab' fragments, pepsin-catalyzed cleavage of anti-CSAp antibody to produce an F(ab')$_2$ fragment and reductive cleavage thereof to form CSAp-specific Fab' fragments, and oxidative coupling of a mixture of said CEA-specific Fab' fragments and sad CSAp-specific Fab' fragments to form F(ab')$_2$ fragments, at least a portion of which are F(ab')$_2$ hybrids specific to both CEA and CSAp.

43. The method of claim 42, wherein said F(ab')$_2$ hybrid is purified by sequential affinity chromatography through a column containing bound CEA and a column containing bound CSAp.

44. An injectable composition, which comprises:
 (a) a marker-specific fragment obtained by cleavage of an antibody specific to a cytoplasmic, intracellular or cell-surface marker substance which is provided or associated with a tumor, said fragment being radiolabeled with a pharmacologically inert radioisotope capable of detection using a photoscanning device; and
 (b) a pharmaceutically acceptable injection vehicle.

45. The composition of claim 44, which further comprises a second marker-specific fragment obtained by cleavage of a second antibody specific to a second tumor-associated marker, said fragment being radiolabeled with a pharmacologically inert radioisotope capable of detection using a photoscanning device.

46. The injectable composition of claim 44, which further comprises a reference fragment which is the corresponding fragment obtained by analogous cleavage of normal immunoglobulin from the same or different species as that used to prepare said specific antibody, said reference fragment being radiolabeled with a different isotope of the same element used to label said marker-specific fragment and emitting at an energy capable of independent detection using said photoscanning device.

47. An injectable composition which comprises:
 (a) an F(ab')$_2$ hybrid formed from two chemically joined Fab' fragments, said fragments being a first marker-specific Fab' fragment obtained by cleavage of an antibody specific to a first tumor-associated marker and a second different marker-specific Fab' fragment obtained by cleavage of a second antibody specific to the same or different tumor associated marker, said hybrid being radiolabeled with a pharmacologically inert radioisotope capable of detection using a photoscanning device; and
 (b) a pharmaceutically acceptable injection vehicle.

48. The injectable composition of claim 47, which further comprises a reference F(ab')$_2$ fragment from normal immunoglobulin from the same or different species as that used to prepare said hybrid, said reference fragment being radiolabeled with a different isotope of the same element used to label said F(ab')$_2$ hybrid and emitting at an energy capable of independent detection using said photoscanning device.

49. A method of tumor radiotherapy, which comprises parenterally injecting into a human subject having a tumor which produces or is associated with a cytoplasmic, intracellular or cell-surface marker substance an effective tumor reducing amount of a marker-specific fragment obtained by cleavage of an antibody specific to said marker substance and radiolabeled with a pharmacologically inert radioisotope capable of detection with a photoscanning device, said labeled fragment further containing in chemical combination an addend containing at least five atoms of boron with at least a natural abundance of Boron-10 isotope; wherein the location of said tumor is determined using said photoscanning device, and a beam of thermal neutrons is then directed at said tumor location.

50. The injectable composition of claim 44, wherein said marker-specific fragment further contains in chemical combination an addend containing at least five atoms of boron with at least the natural abundance of Boron-10 isotope.

* * * * *